United States Patent
Smith et al.

(10) Patent No.: US 7,344,707 B2
(45) Date of Patent: Mar. 18, 2008

(54) LOW COMBUSTION AEROSOL PRODUCTS IN PLASTIC PACKAGES HAVING A REDUCED FIRE HAZARD CLASSIFICATION THAT SUBSEQUENTLY REDUCES STORAGE COSTS

(75) Inventors: Scott Edward Smith, Cincinnati, OH (US); David Frederick Swaile, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/146,191

(22) Filed: May 15, 2002

(65) Prior Publication Data

US 2003/0215399 A1    Nov. 20, 2003

(51) Int. Cl.
- A61K 8/18    (2006.01)
- A61K 8/28    (2006.01)
- A61K 8/58    (2006.01)
- A61K 8/26    (2006.01)
- A61K 8/02    (2006.01)

(52) U.S. Cl. ............ 424/65; 424/47; 424/66; 424/68; 424/401

(58) Field of Classification Search ........ 424/400, 424/401, 47, 65, 66, 68; 206/823; 516/8
See application file for complete search history.

(56) References Cited

U.S. PATENT DOCUMENTS

| | | | |
|---|---|---|---|
| 2,693,983 A | | 11/1954 | Howell |
| 2,746,796 A | | 5/1956 | St. Germain |
| 3,323,206 A | | 6/1967 | Clark |
| 3,378,169 A | | 4/1968 | Clark |
| 4,230,243 A | * | 10/1980 | Spitzer et al. ......... 222/402.18 |
| 4,359,456 A | | 11/1982 | Gosling et al. |
| 4,431,120 A | | 2/1984 | Burger |
| 5,224,630 A | | 7/1993 | Pope et al. |
| 5,516,504 A | | 5/1996 | Tomlinson |
| 5,553,753 A | * | 9/1996 | Abplanalp .................. 222/387 |
| 5,814,309 A | * | 9/1998 | Panitch ........................ 424/65 |
| 5,935,554 A | | 8/1999 | Tomlinson |
| 6,045,784 A | * | 4/2000 | Ruebusch et al. ............ 424/65 |
| 6,270,784 B1 | | 8/2001 | Mrusek et al. |
| 6,315,985 B1 | | 11/2001 | Wu et al. |
| 6,482,783 B1 | | 11/2002 | Lewis et al. |
| 6,485,715 B1 | * | 11/2002 | Smith et al. ................. 424/65 |
| 6,752,983 B1 | * | 6/2004 | Dobbs et al. .............. 424/70.1 |
| 6,783,027 B2 | | 8/2004 | Hilvert et al. |
| 2002/0071810 A1 | | 6/2002 | Wu et al. |
| 2003/0129142 A1 | | 7/2003 | Schroeder et al. |

FOREIGN PATENT DOCUMENTS

| | | |
|---|---|---|
| DE | 19605773 A1 | 2/1997 |
| DE | 10012492 A1 | 9/2001 |
| EP | 0006739 A1 | 1/1980 |
| EP | 0061495 | 10/1982 |
| EP | 0591195 | 4/1994 |
| EP | 0372011 B1 | 6/1995 |
| EP | 0845944 B1 | 11/2000 |
| EP | 1106171 A1 | 6/2001 |
| EP | 1237533 | 9/2002 |
| GB | 1341126 A * | 12/1973 |
| GB | 1347950 | 2/1974 |
| GB | 1482714 A | 8/1977 |
| GB | 1588463 A * | 4/1981 |
| GB | 2214891 A * | 9/1989 |
| JP | 01-272518 | 10/1989 |
| JP | 02-032190 | 2/1990 |
| JP | 02-307556 | 12/1990 |
| JP | 2002-012277 | 1/2002 |
| WO | WO8201176 | 4/1982 |
| WO | WO-9204419 A1 | 3/1992 |
| WO | WO-9618378 A2 | 6/1996 |
| WO | WO-9706687 A1 | 2/1997 |
| WO | WO-0078286 A1 | 12/2000 |
| WO | WO-0124835 A2 | 4/2001 |
| WO | WO-0141728 A1 | 6/2001 |
| WO | WO-0168793 A1 | 9/2001 |

OTHER PUBLICATIONS

The Aerosol Handbook 2nd Ed., Montfort Johnson, Wayne Dorland Company, 1982, Chapter 4, pp. 137-148.

* cited by examiner

*Primary Examiner*—Sreeni Padmanabhan
*Assistant Examiner*—Marina Lamm
(74) *Attorney, Agent, or Firm*—Jack L. Oney; Vladimir Virenberg; Andrew J. Hagerty

(57) ABSTRACT

A low combustion aerosol antiperspirant product in a plastic package having a reduced fire hazard classification. The low combustion product has a chemical heat of combustion equal or less than about 30 kJ/g. The plastic package is made of plastic. The plastic package is capable of containing and dispensing the low combustion product. The plastic package is stable when containing the product and together they have a fire hazard classification of 1 or 2. The low combustion aerosol product may be an anhydrous antiperspirant product.

11 Claims, No Drawings

LOW COMBUSTION AEROSOL PRODUCTS IN PLASTIC PACKAGES HAVING A REDUCED FIRE HAZARD CLASSIFICATION THAT SUBSEQUENTLY REDUCES STORAGE COSTS

TECHNICAL FIELD

The present invention relates to low combustion aerosol products in plastic packages having a reduced fire hazard classification which subsequently reduces storage costs. Such products as antiperspirants can now be sold and warehoused in plastic aerosol containers in a more safe and economic manner.

BACKGROUND OF THE INVENTION

Aerosol products are well known in the art and have good consumer acceptance based on their ability to deliver a material to a surface in a convenient, hygienic manner. This benefit has made aerosols, the product form of choice for antiperspirants for many of the world's consumers. Aerosol antiperspirants deliver a fine spray of antiperspirant that can completely cover the axilla and provide a cool and dry sensation during application.

Typically aerosol antiperspirant products are in the form of a liquid or solid-in-liquid suspensions that are contained under pressure in a metal canister and delivered at a controlled flow rate via a sealing valve. The product is usually delivered by depressing an actuator or similar mechanism, which opens the valve, and then the pressured product is forced through the valve. Pressure is created in the canister by the inclusion of a gas or liquefied gas propellant in the product canister. The propellant can be an integral part of the product or simply create pressure in the headspace above the product. Common propellants include liquefied gases such as butane, isobutane, propane, dimethyl ether, and 1,1 difluoroethane.

These aerosol products (e.g., aerosol antiperspirants) can be highly flammable and can create a substantial fire hazard during storage. In a fire, aerosol canisters can rupture or BLEVE (boiling liquid expanding vapor explosion) and release flammable components such as propellant, hydrocarbons, alcohols, or other flammable compounds, which can then be ignited by the fire thus resulting in further spreading of the flames. Furthermore, some aerosols when exposed to fire have been known to rupture and "rocket with trailing burning liquid" away from their original position and spread the fire to previously unaffected areas. The fire hazard of an aerosol product is shown by its hazard category. Hazard categories of Level 1, 2, and 3 are based on the amount and type of flammable material in the product. More specifically, if a product has a chemical heat of combustion that is from 0 to 8,600 Btu/lb (20 kJ/g), then the product is classified as a Level 1. Similarly, if a product has a chemical heat of combustion that is from 8,600 Btu/lb (20 kJ/g) to 13,000 Btu/lb (30 kJ/g), then the product is classified as a Level 2. Lastly, if a product has a chemical heat of combustion that is greater than 13,000 Btu/lb (30 kJ/g), then the product is classified as a Level 3.

The fire hazard classification of an aerosol product is used to determine proper storage conditions. These storage conditions include necessary sprinkler design, storage height, and secondary container. Level 1 products have the least stringent storage conditions. Level 2 and 3 products have storage requirements that are more commensurate with their increased risk. Level 3, having the most risk, has the most stringent and expensive requirements. These stringent storage conditions increase the cost and the complexity of merchandizing aerosol products. Storage regulations are described in detail in "NFPA 30B Code for the Manufacture and Storage of Aerosol Products 1998 Edition", and is hereby incorporated by reference.

Typically, aerosol products are contained in metal canisters made of aluminum or tin plate. These canisters have a good mechanical strength and heat resistance that significantly reduce the fire hazard by providing a substantial barrier between the flammable product and fire. Metal canisters are often capable of containing products with pressures as high as several hundred PSI so the temperature at which the canister fails and BLEVE occurs can be quite high. Moreover the metals that these canisters are composed of typically have melt temperatures that are greater than 400° C.; therefore, they are not subject to failure due to melting at relatively low fire temperatures (below 200° C.).

It has long been desirable to develop plastic packaging for aerosol products. Moving from metal to plastic provides several benefits such as increased freedom in developing unique canister shapes, developing clear packages, and lowering manufacturing costs. Unfortunately, these plastic packages have shown poor manufacturing and storage stability. Many of these packages are degraded by the product components resulting in package discoloration, swelling, loss of pressure, and in some extreme cases the packages burst during the filling process. Recent development of plastic materials with the necessary physical strength and chemical resistance has finally allowed the development of commercial plastic aerosol packages. Unfortunately, these recently-developed materials typically have a melt point or glass transition temperature less than 200° C.; therefore, it is possible for these packages to fail at lower temperatures than metal canisters and thereby create an increased fire hazard during warehousing as compared to metal canisters. The simplest route to reducing fire hazard is to include water in the product. In fact, the use of plastic packages is preferred when formulating with aqueous solution of antiperspirant active since metal packages often corrode when in contact with these solutions. Unfortunately, water is known to degrade some antiperspirant actives so often it is preferable to formulate anhydrous products.

Since current plastic packages provide a less substantial barrier between the flammable aerosol product and a fire as compared to metal canisters, it is desirable to formulate products for these plastic packages that have a reduced fire hazard classification of level 1 or 2 in order to reduce the overall fire hazard classification of the product package combination. This can be achieved by proper choice of propellant type and level, product solvent type and level, and amount and type of inert ingredient(s).

Typically, aerosol antiperspirants contain 30-85% of a hydrocarbon propellant and thus often have a fire hazard rating of 3. It is the intent of this invention to provide aerosol products that when formulated in stable plastic package provide a level 1 or level 2 fire hazard classifications.

SUMMARY OF THE INVENTION

The present invention provides a low combustion aerosol antiperspirant product in a plastic package having a reduced fire hazard classification. The low combustion product has a chemical heat of combustion equal or less than about 30 kJ/g. The plastic package is capable of containing and dispensing the low combustion product. The plastic package is stable when containing the product and together they have a fire hazard classification of 1 or 2. The low combustion aerosol product may be an anhydrous antiperspirant product.

DETAILED DESCRIPTION OF THE INVENTION

The aerosol antiperspirants of the present invention comprise a product formula with a fire hazard of level 1 or level 2 are contained in a stable plastic package. These and other essential elements or limitation of the product formula with a fire hazard of level 1 or level 2 and are a stable plastic package are described in detail hereinafter.

The term "anhydrous" as used herein, unless otherwise specified, refers to those compositions or materials containing less than about 5%, more preferably less than about 3%, even more preferably less than about 1%, even more preferably zero percent, by weight of free or added water.

The term "ambient conditions" as used herein refers to surrounding conditions at about one atmosphere of pressure, at about 50% relative humidity, and at about 25° C.

"Stable packages" are defined based on their behavior upon storage at 49° C. for 4 weeks. A stable package will not show visible discoloration or hazing upon said storage or have more than 1.5% weight loss or show more than a 2% change in a given dimension (i.e. diameter, width, depth, length, or crimp height) or rupture or BLEVE.

The term "aerosol antiperspirant" as used herein means any packaged antiperspirant composition that is pressurized from a gas or liquefied gas propellant, wherein the propellant provides a way for pushing or moving the antiperspirant composition to and/or through an application device. These aerosol products can deliver the antiperspirant product to the axillia in various ways including, but not limited to, a spray or via a porous application surface that is rubbed on the skin.

The term "plastic" refers to any synthetic or organic materials that can be molded or shaped, generally when heated, and then hardened into a desired form including, but not limited to, polymers, resins, and cellulose derivatives.

The term "plastic package" refers to the container vessel of the aerosol package being made substantially of plastic. The sealing valve and actuator of the package may or may not necessarily be made substantially of plastic.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The pressurized antiperspirant compositions of the present invention can comprise, consist of, or consist essentially of the essential elements and limitations of the invention described herein, as well as any additional or optional ingredients, components, or limitations described herein or otherwise useful in pressurized antiperspirant applications.

Propellant

The aerosol antiperspirant compositions of the present invention comprise a propellant that creates enough pressure to force the product from the canister for application. Products of the instant invention typically have an internal package pressure from about 10 PSIG to about 80 PSIG. Pressure level may be controlled by the type and level of propellant used.

The propellant component of the aerosol antiperspirant compositions of the present invention may contain any known propellant that is compatible with the formulation and package of choice. Preferred propellants are generally in the form of liquefied gases when formulated into the antiperspirant compositions and include dimethylether, 1,1 difluoroethane, 1,1,1,2 tetrafluoro ethane, butane, isobutane, propane, isopentane, pentane or combinations thereof. Dimethyl ether or combination of dimethylether and hydrocarbon propellants are preferred for products that are a single-phase, liquid antiperspirant. Hydrocarbon propellants such as butane, isobutane, propane, isopentane, pentane are preferred for products that are solid in liquid suspensions or emulsion products. The total propellant concentration in the antiperspirant compositions of the present invention ranges from about 5% to about 99%, more typically from about 15% to about 90%, even more preferably from about 20% to about 70%, by weight of the composition. Other suitable propellants include nitrous oxide, carbon dioxide, and halogenated hydrocarbons such as triclorofluoromethane, diclorodifluoromethane, diclorotetrafluoroethane trichlorotrifluoroethane, trichlorotetrafluoroethane, and monochlorodifluoromethane, and combinations thereof.

Antiperspirant Active

The aerosol antiperspirant compositions of the present invention comprise a antiperspirant active suitable for application to human skin. The concentration of antiperspirant active in the composition should be sufficient to provide the finished antiperspirant product with the desired perspiration wetness and odor control. For liquid aerosol antiperspirant products the active is dissolved in a solvent such as water, ethanol or a liquid polyol. For anhydrous liquid antiperspirant products, the active is preferably solubilized in a liquid polyol solvent. For products that are a solid in liquid suspension the active is preferably delivered as a powder.

Antiperspirant active concentrations in the aerosol antiperspirant compositions preferably range from about 0.1% to about 26%, more preferably from about 1% to about 20%, even more preferably from about 2% to about 10%, by weight of the composition. All such weight percentages are calculated on an anhydrous metal salt basis exclusive of water and any complexing or buffering agent such as glycine, glycine salts, or other complexing or buffering agent.

The antiperspirant active for use in the antiperspirant compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are salts such as aluminum halides, aluminum chlorohydrate, aluminum hydroxyhalides, zirconyl oxyhalides, zirconyl hydroxyhalides, and mixtures thereof. Aluminum salts are most preferred for non-contact pressurized compositions.

Preferred aluminum salts for use in the antiperspirant compositions include those that conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide" wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, and Gosling et al., issued Nov. 16, 1982, all of which are incorporated herein by reference. Mixtures of aluminum salts are described in British Patent Specification 1,347,950, Shin et al., published Feb. 27, 1974.

Zirconium salts for use in the antiperspirant compositions, especially in pressurized contact forms, include those which conform to the formula:

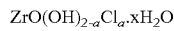

wherein a is any number having a value of from 0 to about 2; x is from about 1 to about 7; and wherein a and x may both have non-integer values. Preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978. Zirconium salts are preferably used in products that deliver the product via an application device that is rubbed on the skin.

Preferred antiperspirant actives for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlorohydrex glycine and combinations thereof.

Preferably the single phase liquid anhydrous antiperspirant compositions of the present invention comprise selected liquid polyols for solubilizing for antiperspirant active material in the composition. The antiperspirant composition preferably comprises from about 1% to about 80%, more preferably from about 2% to about 60%, even more preferably from about 3% to about 20%, by weight of the selected liquid polyols.

The preferred liquid polyols for use in the pressurized antiperspirant composition of the present invention are selected to have at least 3 carbon atoms and adjacent hydroxy-substituted carbon atoms at the α and β positions of the liquid polyol. The preferred liquid polyols for use in the compositions are those that conform to the formula:

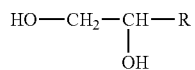

wherein R is an amide, ester, alkyl, ether or silicone-containing moiety, each moiety containing at least 1 carbon atom. The R group is preferably an alkyl or ether group, more preferably an alkyl group having from about 1 to about 10 carbon atoms, more preferably from about 2 to about 6 carbon atoms. The liquid polyols preferably have either 2 or 3 hydroxyl groups in total.

The R group on the preferred liquid polyol can therefore be substituted or unsubstituted, branched or straight or cyclic, saturated or unsaturated. Non limiting examples of suitable substituents include hydroxyl groups, amines, amides, esters, ethers, alkoxylate groups (e.g., ethoxylates, propoxylates, etc.) and so forth.

Non limiting examples of the preferred liquid polyols for use in the pressurized compositions of the present invention include 1,2-propylene glycol, glycerin, 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and combinations thereof.

Non limiting examples of solubilized antiperspirant active for use in the pressurized antiperspirant compositions of the present invention, and methods of making the solubilized active, are described in U.S. Pat. No. 6,149,897 (Swaile); U.S. Pat. No. 6,126,928 (Swaile); and U.S. Pat. No. 5,968,489 (Swaile et al.), which descriptions are incorporated herein by reference. Other non limiting examples of solubilized antiperspirant active and methods of making it are described in EP 0 404 533 (Smith et al.).

Carrier Liquids

The aerosol antiperspirant products of the current invention will typically include a carrier liquid to help deliver the antiperspirant active to skin surface in a cosmetically acceptable manner. Suitable carrier liquids for use in the aerosol antiperspirant compositions of the present invention include any silicone or silicone-containing material that is known or otherwise suitable for topical application to the skin, provided that the silicone or silicone-containing material is a liquid under ambient conditions or is otherwise in liquid form within the pressurized antiperspirant compositions of the present invention.

The concentration of the silicone liquid in the composition preferably ranges from about 0.1% to about 50%, more preferably from about 1% to about 25%, more preferably from about 2% to about 15%, by weight of the pressurized antiperspirant composition.

Non limiting examples of suitable volatile silicones are described in Todd et al., "Volatile Silicone Fluids for Cosmetics", Cosmetics and Toiletries, 91:27-32 (1976), which descriptions are incorporated herein by reference. Preferred among these volatile silicones are the cyclic silicones having from about 3 to about 7, more preferably from about 5 to about 6, silicon atoms. Most preferably are those that conform to the formula:

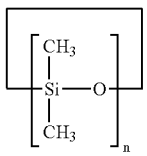

wherein n is from about 3 to about 7, preferably from about 5 to about 6, most preferably 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof. Cyclopentasiloxane is most preferred among the volatile silicone liquids.

Non limiting examples of non volatile silicone liquids for use in the aerosol antiperspirant compositions of the present invention include those which conform to either of the formulas:

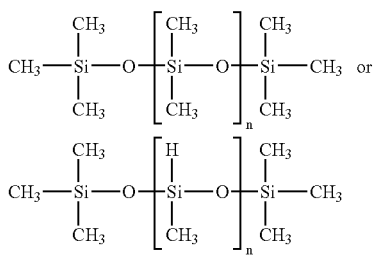

wherein n is greater than or equal to 1. These linear silicone materials will generally have viscosity values of from about 10 centistoke to about 100,000 centistoke, preferably less than about 500 centistoke, more preferably from about 10 centistoke to about 200 centistoke, even more preferably from about 10 centistoke to about 50 centistoke, as measured under ambient conditions. Non limiting examples of non-volatile, linear silicones suitable for use in the antiperspirant compositions include but are not limited to, Dow Corning 200, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

Other silicone liquids as carrier liquids for use in the aerosol antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 *Cosmetics, Science and Technology* 27-104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Other non silicone based carrier liquids can also be employed in the instant invention to provide different skin feel options. Some of these may also include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Preferably such liquid carriers are also water-immiscible liquids under ambient conditions. Other suitable water-immiscible, polar organic liquid carriers or solvents for use in combination with the 1,2-hexanediol are described in Cosmetics, Science, and Technology, Vol. 1, 27-104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other liquid carriers for use in the instant invention include water-miscible, polar organic liquid carriers or solvents, examples of which include short chain alcohols such as ethanol and glycol solvents such as propylene glycol, hexylene glyol, dipropylene glycol, tripropylene glycol, and so forth. Other suitable similar solvents also include polyalkoxylated carriers such as polyethylene glycols, polyproylene glycols, combinations and derivatives thereof, and so forth. Non-limiting examples of polar solvents suitable for use herein are described in U.S. Pat. No. 5,429,816.

Optional liquid carriers for use in the instant invention may also include non-polar carriers such as mineral oil, petrolatum, isohexadecane, isododecane, various hydrocarbon oils such as the Isopar or Norpar series available from Exxon Corp. or Permethyl series available from Persperse, and the Soltrol series available from Phillips Chemical, and any other polar or non-polar, water-miscible, organic carrier liquid or solvent known or otherwise safe and effective for topical application to human skin.

Other optional liquid carriers for use in combination with the composition include fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47-62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress.RTM. PFPE oils, and the series fluorosurfactants from Dupont Performance Chemicals under the trade name Zonyl.RTM. Fluorosurfactants.

Package

The antiperspirant aerosol products of the current invention are delivered from a total package with consisting of a delivery device, a valve to control flow and a stable plastic package that holds the product when sealed using said valve. The deliver device can be any known deliver device including but not limited to a button actuator and a porous sintered dome. Likewise any known valve that is capable of sealing the pressurized product within the plastic package and being easily opened and closed to control the release of the product to the delivery device. Both the delivery device and valve can be made of any material including but not limited to metal, plastic or glass.

The stable plastic package used in the instant invention can be made of any known plastic that is capable of containing the pressurized product and that does not interact with package in such a way that it alters the composition of the product or changes the appearance of the plastic or reduces the physical strength or dimensions of the package, or reduces the ability of package to contain the pressurized product. The package can be made of any know plastic that can be shaped or molded into a bottle and sealed with a valve. Suitable plastics include polyester, polyamide, polycarbonate, polyoxymethylene, polyacrylonitrile, polyoelofin, or fluoropolymers and other plastics suitable for molding into a container. It is preferred in this invention that that the preferred package material be amorphous nylon and more specifically an amorphous nylon 6 due to it high chemical resistance, thermal quality and mechanical strength.

Optional Ingredients

The pressurized antiperspirant compositions of the present invention may further comprise other optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Non limiting examples of optional ingredients include preservatives, deodorant antimicrobials, fragrances, deodorant perfumes, coloring agents or dyes, thickeners, pH modifiers, surfactants and other wash-off aids, co-solvents, emollients or residue masking liquids other than the silicone liquids described herein, pharmaceutical actives, vitamins, and combinations thereof. Preferred optional ingredients include dimethicone copolyols.

Assigning Fire Hazard

The fire hazard classification of an aerosol product is based upon the chemical heat of combustion of the antiperspirant composition, $\Delta H_{c(product)}$. The chemical heat of combustion of the antiperspirant composition, $\Delta H_{c(product)}$ may be calculated based on the chemical heat of combustion of each of the ingredients within said antiperspirant composition.

The chemical heat of combustion for each ingredient, $\Delta H_{c(I)}$, is equal to the multiplication of the theoretical heat of combustion, $\Delta H_{comb(I)}$, and the combustion efficiency, $\chi_{(I)}$.

$$\Delta H_{c(I)} = \chi_{(I)} * \Delta H_{comb(I)}$$

Heats of combustion for a variety of ingredients are available from standard chemical and chemical engineering references, such as *Perry's Chemical Engineers' Handbook*, and other standard references, such as the *Fire Protection Handbook* and the *SFPE Handbook of Fire Protection Engineering*. The combustion efficiency, $\chi_{(I)}$ is usually less than 1, and more particularly equal to 0.95.

Once we have calculated the chemical heat of combustion for each ingredient, the chemical heat of combustion for the antiperspirant composition may also be calculated as the summation of the weighted heats of combustion for the individual components as follows:

$$\Delta H_{c(product)} = \Sigma(I\% * \Delta H_{c(I)})$$

where $\Delta H_{c(product)}$=chemical heat of combustion of the antiperspirant composition (kJ/g)

I %=weight percent of a particular component I in the antiperspirant composition (w/w %)

$H_{c(I)}$=chemical heat of combustion of component I (kJ/g)

Heats of combustion for an ingredient may also be determined by calculation or by appropriate test methods, such as ASTM D 240, *Standard Test Method for Heat of Combustion of Liquid Hydrocarbon Fuels by Bomb Calorimeter*. Further, heats of combustion can be estimated from structural isomers when available. Where the chemical heat of combustion of a particular ingredient is not readily available, or if the ingredient is a minor ingredient of the antiperspirant composition, use a theoretical heat of combustion equal to 19,000 Btu/lb (43.7 kJ/g), which is a typical value for hydrocarbons.

An example of how to calculate the chemical heat of combustion of an antiperspirant composition, $\Delta H_{c(product)}$, follows:

EXAMPLE A

| Ingredients | (a) I % Weight (w/w %) | (b) $H_{c(I)}$ of Ingredient (kJ/g) | = (a) * (b) |
|---|---|---|---|
| Dimethyl ether | 40 | 26.5 | 10.6 |
| Aluminum chlorohydrate in propylene glycol (20% anhydrous solution) | 40 | 16.4* | 6.6 |
| Ethanol | 19 | 24.5 | 4.7 |
| Fragrance, etc. | 1 | 43.7** | 0.4 |
| | | $\Delta H_{c(product)}$ | $\Sigma$ = 22.3 kJ |

*$H_{c(I)}$ Of Ingredient (kJ/g) of solution is determined by multiplying $H_{c(I)}$ of Ingredient (kJ/g) of propylene glycol (20.5 kJ/g) by 0.8 to account for 20% aluminum chlorohydrate in solution. Aluminum chlorohydrate is inert and does not contribute to $H_{c(I)}$ of Ingredient (kJ/g).
**minor ingredient using a theoretical heat of combustion equal to 19,000 Btu/lb (43.7 kJ/g)

Since Example A has a chemical heat of combustion, $\Delta H_{c(product)}$ of 23.9 kJ, which is less than 30 kJ (see above), then Example A would have a fire hazard classification of a Level 2.

Formulating Aerosol Antiperspirants in Stable Plastic Packages Having Level 1 and Level 2 Fire Hazards Although there are many ways known in the art to formulate aerosol antiperspirant products, when formulating an antiperspirant aerosol products with level 1 and level 2 fire hazard classifications for use in stable plastic packages there are several considerations that have not be appreciated by the prior art. Several non-limiting techniques for formulating these products are as follows.

One method of formulating an aerosol antiperspirant product in a stable plastic package with a level 1 or level 2 fire hazard is to control the propellant type and level used in the composition. Often the propellant in an aerosol antiperspirant is the largest contributor to the heat of combustion, therefore, choice of propellant type and level can be critical to achieving a level 1 or level 2 fire hazard. Lower heat of combustion propellants such as dimethyl ether, carbon dioxide, nitrous oxide, 1,1 difluoroethane, and 1,1,1,2 tetrafluoroethane are preferred propellants. These preferred propellants are best if used at levels of 5 to 50% and most preferred at level of 10 to 40%. Higher heat of combustion propellants, such as hydrocarbons (e.g., butane, isobutane, pentane, isopentane, and propane) may also be used but preferably at lower percentages like 5 to 25%. These higher heat of combustion propellants may be used at higher percentages (e.g., up to about 40%) if the remainder of the composition comprises most inert materials and/or ingredients with very low heat of combustion. The formulated composition may include a blend of lower and higher heat of combustion propellants to control the internal pressure of the product while still reducing the fire hazard classification of the composition.

Another method of formulating an aerosol antiperspirant product in a stable plastic package with a level 1 or level 2 fire hazard is to substitute silicone-based carrier liquids for hydrocarbon-based carrier liquids. Silicone-based carrier liquids (including, but not limited to, cyclopentasiloxane, dimethicone, and dimethicone copolyol) have relatively low heats of combustion as compared to hydrocarbon materials (including, but not limited to, isopropyl myristate, isopropyl palmitate, isododecane, polyisobutene and mineral oil) that are commonly found in aerosol antiperspirant products. Often it is advantageous not to include any hydrocarbon carrier liquid, although if used (for example up to about 20%), the product may be formulated to include lower propellant levels and/or high levels of inert ingredients to reduce the fire hazard.

Another method of formulating an aerosol antiperspirant product in a stable plastic package with a level 1 or level 2 fire hazard is to formulate with high antiperspirant active levels. Many of the anhydrous aerosol antiperspirant products in the art use a relatively low active level 1-5% and deliver the necessary amount of active to the axilla via a relatively large product dose (e.g., 1 to 3 grams per axilla). Antiperspirant active typically has a very low heat of combustion and often are inert; therefore, to lower the overall heat of combustion for the product, it is a recommendation of this invention within this example to use relatively high active levels (e.g., from about 5 to about 25%) and relatively low product dose (from about 0.1 gram to about 1 gram).

Another method of formulating an aerosol antiperspirant product in a stable plastic package with a level 1 or level 2 fire hazard is to eliminate product package interactions that will cause the package to become unstable. The design of a plastic package includes the choice of material and dimensional/structural considerations (e.g., wall thickness, angles/radius of corners, etc). The packaging material selected may be based on its compatibility with the product composition, more particular the propellant type and level. High levels (e.g., greater than 20% of aggressive propellants, like DME) require the use of chemically resistant packages made with materials like amorphous nylon. Other plastic materials such as PET can be employed with other propellants such as butane, carbon dioxide, nitrous oxide and/or lower levels of propellant.

While the above formulation methods are intended to provide helpful techniques to the manufacturer of such products, the present invention is not limited to said methods. Nor is it the intent of the present invention to require the implementation of each and/or all the above methods, rather one skilled in the art would appreciate that a variety of these inventive methods may be used to achieve the benefits of the present invention.

Additional Examples of Aerosol Antiperspirants

| Ingredients | $H_{c(l)}$ of Ingredient (kJ/g) | B | D | E | F |
|---|---|---|---|---|---|
| Aluminum chlorohydrate in 1,2 hexanediol (20% anhydrous solution) [3] | 22.8 [3] | 25% | | 30% | |
| Aluminum zirconium trichlorohydrate gly in 1,2 hexanediol (20% anhydrous solution) [3] | 22.8 [3] | | 30% | | 30% |
| Aluminum chlorohydrate powder | 0 | | | | |
| Aluminum chlorohydrate in water (40% anhydrous solution) | 0 | | | | |
| Isopropyl myristate | 36.2 | | | | |
| Quatemium 18 Hectorite | 0 | | | | |
| Propylene Carbonate | 43.3 [4] | | | | |
| Dimethicone copolyol [5] | 27 | 8.3% | 40% | 25% | 10% |
| Dimethiconol [6] | 27 | | | 25% | |
| Dimethicone (10 Cst) [7] | 27 | 11.7% | | | |
| PEG-8 | 24.6 | | 10% | | |
| Ethanol | 24.7 | 8% | | | 10% |
| Propylene glycol | 20.5 | | | | |
| Cyclopentasiloxane | 25.1 | | | | 30% |
| Cyclopentasiloxane and dimethicone copolyol [8] | 26.3 | 5% | | | |
| Fragrance | 43.3 [4] | 2% | | | |
| Butane | 43.3 | | 20% | 10% | |
| Dimethl ether | 26.5 | 40% | | 10% | 20% |
| 1,1,2 tetrafluoro ethane | 0 | | | | |

| | | | | | |
|---|---|---|---|---|---|
| $\Delta H_{c(product)}$ | | 25.9 | 28.7 | 27.4 | 24.7 |
| Package Material | | Nylon | Nylon | Nylon | Nylon |
| Fire hazard level | | 2 | 2 | 2 | 2 |

| Ingredients | G | H | I | J | k$^{(1)}$ | l$^{(2)}$ |
|---|---|---|---|---|---|---|
| Aluminum chlorohydrate in 1,2 hexanediol (20% anhydrous solution) $^{(3)}$ | 25% | | | | 25% | |
| Aluminum zirconium trichlorohydrate gly in 1,2 hexanediol (20% anhydrous solution) $^{(3)}$ | | 30% | | | | |
| Aluminum chlorohydrate powder | | | 30% | | | 10% |
| Aluminum chlorohydrate in water (40% anhydrous solution) | | | | 30 | | |
| Isopropyl myristate | | | 3% | | | 1% |
| Quaternium 18 Hectorite | | | 0.25% | | | 1.5% |
| Propylene Carbonate | | | 0.08% | | | 0.5% |
| Dimethicone copolyol $^{(5)}$ | 8.3% | 10% | | | 8.3% | |
| Dimethiconol $^{(6)}$ | | | | | | |
| Dimethicone (10 Cst) $^{(7)}$ | 20.7% | | 3% | | 20.7% | 0.5% |
| PEG-8 | | | | | | |
| Ethanol | | 10% | | | | |
| Propylene glycol | | | | 40% | | |
| Cyclopentasiloxane | | 30% | 23.07% | | | 25.9% |
| Cyclopentasiloxane and dimethicone copolyol $^{(8)}$ | 5% | | | | 5% | |
| Fragrance | 1% | | 0.6% | | 1% | 0.6% |
| Butane | | | | | | 60% |
| Dimethyl ether | 40% | | 40% | 30 | 40% | |
| 1,1,1,2 tetrafluoro ethane | | 20% | | | | |
| $\Delta H_{c(product)}$ | 26.9 | 19.4 | 18.6 | 16.2 | 25.8 | 33.5 |
| Package Material | Nylon | Nylon | Nylon | Nylon | PET | Nylon |
| Fire hazard level | 2 | 1 | 1 | 1 | 2 | 3 |

Examples A-G are clear, single-phase antiperspirant compositions made in clear nylon packages and are non-limiting examples of the present invention. Example H is a solid in liquid suspension formulation made in a nylon package and is also a non-limiting example of the present invention.
(1) Example K is a comparative example. The package material used in this example is not compatible with the antiperspirant composition and is thus unstable. This package shows visible whitening, more than 5% weight loss, and/or more than a 5% expansion in the diameter of the package.
(2) Example L is a comparative example. The $\Delta H_{c(product)}$ for this product is more than 30 kJ/G and thus has a fire hazard rating of 3.
(3) $H_{c(I)}$ of Ingredient (kJ/g) of solution is determined by multiplying $H_{c(I)}$ of Ingredient (kJ/g) of hexane diol (28.5 kJ/g) by 0.8 to account for 20% aluminum chlorohydrate or aluminum zirconium trichlorohydrate gly in solution. Aluminum chlorohydrate and aluminum zirconium trichlorohydrate gly are inert and do not contribute to $H_{c(I)}$ of Ingredient (kJ/g).
(4) Minor ingredients use a theoretical heat of combustion equal to 19,000 Btu/lb (43.7 kJ/g).
(5) DC 5202 supplied by Dow Corning, Midland Michigan. Hc(I) of Ingredient (kJ/g) provided by supplier.
(6) DC supplied by Dow Corning, Midland Michigan. $H_{c(I)}$ of Ingredient (kJ/g) provided by supplier.
(7) DC 200 fluid supplied by Dow Corning, Midland Michigan. $H_{c(I)}$ of Ingredient (kJ/g) provided by supplier.
(8) DC 5225 supplied by Dow Corning, Midland Michigan. $H_{c(I)}$ of Ingredient (kJ/g) provided by supplier.

What is claimed is:

1. A low combustion aerosol antiperspirant product in a plastic package having a reduced fire hazard classification, comprising:
   a) a low combustion antiperspirant product comprising:
      i) from about 5% to about 30%, by weight of the product, of an antiperspirant active dissolved in a solvent other than water;
      ii) from about 26% to about 50%, by weight of the product, of a silicone-containing carrier liquid;
      iii) either from about 5% to about 50%, by weight of the product, of a propellant selected from the group consisting of dimethyl ether, carbon dioxide, nitrous oxide, 1,1 difluoroethane, 1,1,1,2 tetrafluaro ethane and mixtures thereof, or from about 5% to about 40%, by weight of the product, of a hydrocarbon type propellant,
   wherein the product has a chemical heat of combustion equal to or less than 30 kJ/g, and wherein the product is substantially devoid of a hydrocarbon carrier liquid; and
   b) a plastic package that is capable of containing and dispensing the product,
   wherein the combination of the product and the plastic package has a fire hazard classification of 1 or 2.

2. The low combustion aerosol product in a plastic package of claim 1, wherien the antiperspirant active is included in an amount from about 25% to about 30%, by weight of the product.

3. The low combustion aerosol product in a plastic package of claim 1, wherein the antiperspirant active is selected from the group consisting of aluminum chlorohydrat, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium ocrachlorohydrex glycine.

4. The low combustion aerosol product in a plastic package of claim 1, wherein the antiperspirant active is selected from the group consisting of aluminum zirconium trichlorohydrate, aluminum zirconium trefrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlorohydrex glycine.

5. The low combustion aerosol product in a plastic package of claim 1, wherein the propellant is selected from the group consisting of dimethyl ether, carbon dioxide, nitrous oxide, 1,1 difluoroethane, 1,1,1,2 tetrafluoro ethane, and mixtures thereof.

6. The low combustion aerosol product in a plastic package of claim 1, wherein the propellant comprises dimethyl ether in an amount from about 30% to about 40%, by weight of the product.

7. The low combustion aerosol product in a plastic package of claim 1, wherein the propellant comprises 1,1,1,2 tetrafluoro ethane.

8. The low combustion aerosol product in a plastic package of claim 1, wherein the propellant comprises carbon dioxide.

9. The low combustion aerosol product in a plastic package of claim 1, wherein the plastic package is made from a material comprising polyester, polyamide, potycarbonate, polyoxmethylene, plyacrylonitrile, polyolefin, and/or fluoropolymers.

10. The low combustion aerosol product in a plastic package of claim 1, wherien the plastic package is made from a material comprising nylon.

11. The low combustion aerosol product in a plastic package of claim 1, wherein the product employs 3% or less of a hydrocarbon carrier liquid.

* * * * *